(12) United States Patent
Allec et al.

(10) Patent No.: US 12,317,024 B2
(45) Date of Patent: May 27, 2025

(54) ELECTRONIC DEVICES WITH SKIN SENSORS

(71) Applicant: Apple Inc., Cupertino, CA (US)

(72) Inventors: Nicholas P. Allec, Santa Cruz, CA (US); Yuta Kuboyama, San Mateo, CA (US); Xiaoyang Zhang, Singapore (SG); Xi Chen, Millbrae, CA (US); Ryan M. Buck, San Francisco, CA (US); Praveesh Chandran, Singapore (SG); Yifei Wang, Sunnyvale, CA (US); Tingjun Xu, San Jose, CA (US)

(73) Assignee: Apple Inc., Cupertino, CA (US)

( * ) Notice: Subject to any disclaimer, the term of this patent is extended or adjusted under 35 U.S.C. 154(b) by 229 days.

(21) Appl. No.: 17/149,552

(22) Filed: Jan. 14, 2021

(65) Prior Publication Data
US 2022/0225006 A1 Jul. 14, 2022

(51) Int. Cl.
*H04R 1/10* (2006.01)
*A61B 5/00* (2006.01)
*G02B 5/28* (2006.01)

(52) U.S. Cl.
CPC ......... *H04R 1/1041* (2013.01); *A61B 5/0059* (2013.01); *A61B 5/441* (2013.01); *A61B 5/681* (2013.01); *A61B 5/6817* (2013.01); *G02B 5/281* (2013.01); *H04R 1/1016* (2013.01); *A61B 2503/12* (2013.01)

(58) Field of Classification Search
CPC .. H04R 1/1041; H04R 1/1016; A61B 5/0059; A61B 5/441; A61B 5/681; A61B 5/6817; A61B 2503/12; A61B 5/02438; A61B 5/02427; A61B 5/02433; A61B 5/72114; G02B 5/281
See application file for complete search history.

(56) References Cited

U.S. PATENT DOCUMENTS

| 6,538,751 | B2 | 3/2003 | No | |
|---|---|---|---|---|
| 8,033,706 | B1 * | 10/2011 | Kelly | G02B 6/0043 362/617 |
| 8,330,840 | B2 * | 12/2012 | Lenchenkov | H01L 27/14621 348/340 |
| 9,526,427 | B2 | 12/2016 | Darty et al. | |
| 9,590,680 | B1 * | 3/2017 | Reuss | H04B 1/385 |
| 10,433,738 | B2 | 10/2019 | Vermeulen et al. | |

(Continued)

*Primary Examiner* — Carolyn R Edwards
*Assistant Examiner* — Kuassi A Ganmavo
(74) *Attorney, Agent, or Firm* — Treyz Law Group, P.C.; G. Victor Treyz; David K. Cole

(57) ABSTRACT

A wearable electronic device such as an earbud, wristwatch, or other device may be provided with a skin sensor. The skin sensor may use optical measurements to detect the presence of skin adjacent to the electronic device. The sensor may have first and second light-emitting devices such as infrared devices that emit light at respective first and second infrared light wavelengths. Reflected light is monitored by a photodetector. Control circuitry can initiate or pause audio playback or take other actions in response to determining from the reflected light measurements that skin is present. The sensor may have a thin-film interference filter or other optical structure that overlaps the first and second light-emitting devices to narrow the angular spread of light emitted from the skin sensor. This reduces tilt sensitivity and helps enhance skin sensor accuracy.

16 Claims, 8 Drawing Sheets

(56) References Cited

U.S. PATENT DOCUMENTS

| | | |
|---|---|---|
| 10,842,393 B2 | 11/2020 | Watanabe |
| 2005/0174664 A1* | 8/2005 | Ito ............... G02B 5/281 |
| | | 359/883 |
| 2007/0064294 A1* | 3/2007 | Hoshino ............ G02B 6/0065 |
| | | 359/237 |
| 2007/0106160 A1* | 5/2007 | Kilgore ............ G06V 40/1394 |
| | | 600/473 |
| 2009/0051284 A1* | 2/2009 | Cok ................ H10K 50/854 |
| | | 313/506 |
| 2009/0318908 A1* | 12/2009 | Van Pieterson ....... A61B 5/443 |
| | | 606/9 |
| 2010/0249550 A1* | 9/2010 | Lovejoy ............. A61B 5/6826 |
| | | 600/323 |
| 2011/0004106 A1* | 1/2011 | Iwamiya ........... A61B 5/02438 |
| | | 600/476 |
| 2012/0197093 A1* | 8/2012 | LeBoeuf ............ A61B 5/7203 |
| | | 250/226 |
| 2014/0016803 A1* | 1/2014 | Puskarich ............... H04R 5/04 |
| | | 381/74 |
| 2015/0243824 A1* | 8/2015 | Bhat ................. H01L 31/167 |
| | | 250/206 |
| 2016/0296172 A1* | 10/2016 | Shi ..................... A61B 5/721 |
| 2016/0377762 A1* | 12/2016 | Uedaira .................. G01V 8/12 |
| | | 250/221 |
| 2017/0007130 A1* | 1/2017 | Spaziani .......... H01L 27/14603 |
| 2017/0055860 A1* | 3/2017 | Vermeulen ......... A61B 5/02438 |
| 2017/0090599 A1* | 3/2017 | Kuboyama .......... H03K 17/962 |
| 2017/0261425 A1 | 9/2017 | Deliwala |
| 2018/0067245 A1* | 3/2018 | Giachino ............... G02B 5/285 |
| 2018/0098701 A1* | 4/2018 | Blomqvist ............. A61B 5/021 |
| 2018/0192876 A1* | 7/2018 | Spaziani ............ A61B 5/0059 |
| 2018/0228414 A1* | 8/2018 | Shao ............... A61B 5/02427 |
| 2019/0079226 A1* | 3/2019 | Downing ............. G03F 7/0015 |
| 2020/0008716 A1* | 1/2020 | Kintz ................... A61B 5/1459 |
| 2020/0397323 A1* | 12/2020 | Ruponen ........... A61B 5/02438 |
| 2021/0368254 A1* | 11/2021 | Kemmerer ............. G06F 3/017 |
| 2022/0160263 A1* | 5/2022 | Lepak ................. A61B 5/1459 |
| 2022/0167864 A1* | 6/2022 | Block ............... A61B 5/02433 |
| 2023/0207606 A1* | 6/2023 | Mezouari ................ H01L 33/42 |
| | | 257/79 |

\* cited by examiner

ELECTRONIC DEVICES WITH SKIN SENSORS

FIELD

This relates generally to electronic devices, and, more particularly, to electronic devices with sensors.

BACKGROUND

Electronic devices often have sensors. For example, sensors may be used in earbuds to help detect when earbuds are being worn in a user's ears. It can be challenging for such sensors to distinguish between scenarios in which earbuds are located in a user's ears and scenarios in which earbuds are located in another confined space such as a user's pocket.

SUMMARY

Electronic devices may be provided with skin sensors. The electronic devices may include ear buds, wristwatches, and other electronic devices.

A skin sensor may use optical measurements to detect the presence of skin adjacent to an electronic device. Actions may be taken by the device in response to detection of the presence of skin. For example, in a pair of earbuds, the initiation of audio playback and the pausing of audio by the earbuds may be controlled based on whether the skin sensor detects skin, indicating that the earbuds are being worn in a user's ears.

A skin sensor may have first and second light-emitting devices such as infrared devices that emit light at respective first and second infrared light wavelengths. Reflected light is monitored by a photodetector. The sensor may have a thin-film interference filter or other optical structures overlapping the first and second light-emitting devices to narrow the angular spread of light emitted from the skin sensor. This reduces tilt sensitivity and helps enhance skin sensor accuracy.

In an illustrative configuration, a thin-film interference filter overlapping the first and second light-emitting devices has a first bandpass filter with a first pass band overlapping the first light-emitting device to pass light from the first light-emitting device and has a second bandpass filter with a second pass band overlapping the second light-emitting device to pass light from the second light-emitting device.

DETAILED DESCRIPTION

Electronic devices may be provided with skin sensors. For example, skin sensors may be included in wearable devices such as earbuds. The skin sensors may be used to detect when the earbuds are located in a user's ears. When it is determined that the earbuds are located in a user's ears, audio may be played for a user. If, on the other hand, skin sensors do not detect the presence of skin, it may be concluded that the earbuds are not in a user's ears so that audio playback can be halted. To help avoid false positives, the skin sensors may use a multi-wavelength design that helps to distinguish between scenarios in which the sensors are located adjacent to skin and scenarios in which the sensors are located next to other materials (e.g., fabric in a user's pocket).

The spectral response of human skin is characterized by peaks and valleys. for example, the reflectivity of human skin is relatively high (e.g., about 50-60%) at a wavelength of 1065 nm and is relatively low (e.g., about 5-10%) at a wavelength of 1465 nm. As a result, the presence of skin can be monitored by a sensor that emits light at 1065 nm and 1465 and that measures the amount of light reflected from a target object at these wavelengths. With an illustrative arrangement, the ratio R of reflected light at 1065 nm to reflected light at 1465 nm can be monitored and compared to a threshold TH (e.g., 2.0 or other suitable value). When the ratio R is less than TH, it can be concluded that the target object is not skin. When the ratio R is greater than TH, it can be concluded that skin is present. To help avoid false positives in the presence of non-skin objects, it may be desirable to control the light output from the skin sensors. In particular, false positives may be suppressed by narrowing the angular spread of emitted light. This may help avoid tilt dependencies in the skin sensor readings.

Figure 1:
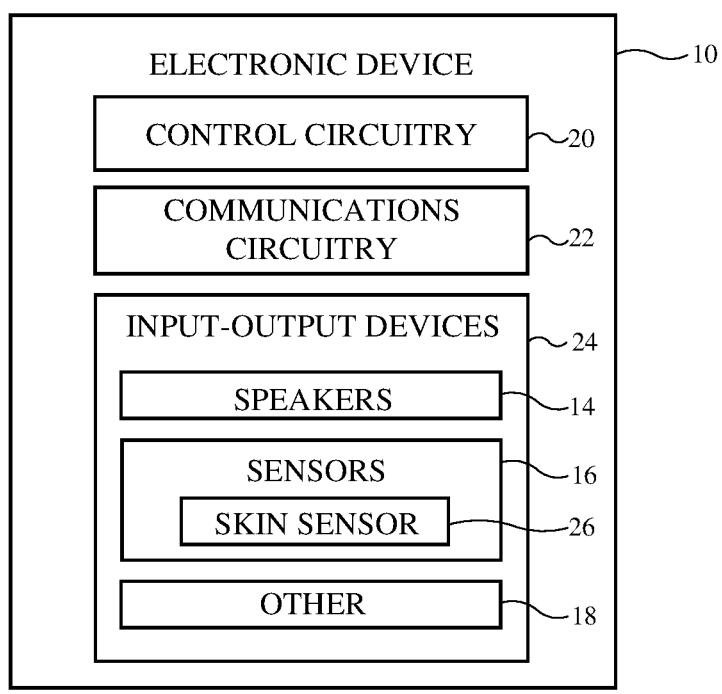
FIG. 1 is a schematic diagram of an illustrative electronic device in accordance with an embodiment.

FIG. 1 is a schematic diagram of an illustrative electronic device of the type that may use a skin sensor. The skin sensor may be used to detect the presence of a human body part that has skin such as an ear, arm, head, or other skin-covered body part. The detected presence of skin may be used to trigger an action such as the presentation of audio through a speaker and/or may be used to activate or inactivate one or more other functions in a device (e.g., turning on or off input-output devices, initiating or halting the presentation of media, adjusting on-screen options on a touch sensitive display, adjusting other user selectable options, etc.).

FIG. 1 is a schematic diagram of an illustrative electronic device. Electronic device 10 may be operated in a system with one or more electronic devices. For example, device 10 may receive media content (e.g., audio and/or video) from a companion device (e.g., a cellular telephone, tablet computer, laptop computer, desktop computer, etc.) or device 10 may be a stand-alone device. Configurations in which device 10 is a stand-alone device may sometimes be described herein as example. Device 10 may be an earbud, a wristwatch, a head-mounted device, or other wearable electronic device. In some arrangements, device 10 may be a portable device such as a cellular telephone, tablet computer, or laptop computer, may be a desktop computer, may be a television, may be an accessory such as a trackpad, computer mouse, computer stylus, or other accessory, or may be any other suitable electronic equipment. Illustrative configurations in which device 10 is an earbud or a wristwatch may sometimes be descried herein as an example.

Device 10 may include control circuitry 20. Control circuitry 20 may include storage and processing circuitry for supporting the operation of device 10. The storage and processing circuitry may include storage such as nonvolatile memory (e.g., flash memory or other electrically-programmable-read-only memory configured to form a solid state drive), volatile memory (e.g., static or dynamic random-access-memory), etc. Processing circuitry in control circuitry 20 may be used to gather input from sensors and other input devices and may be used to control output devices. The processing circuitry may be based on one or more microprocessors, microcontrollers, digital signal processors, baseband processors and other wireless communications circuits, power management units, audio chips, application specific integrated circuits, display control circuits, etc. During operation, control circuitry 20 may use a display and/or other output devices in providing a user with visual output and/or other output.

To support communications between device 10 and external equipment, control circuitry 20 may communicate using communications circuitry 22. Circuitry 22 may include antennas, radio-frequency transceiver circuitry (wireless transceiver circuitry), and other wireless communications circuitry and/or wired communications circuitry. Circuitry 22, which may sometimes be referred to as control circuitry and/or control and communications circuitry, may support bidirectional wireless communications between device 10 and external equipment over a wireless link (e.g., circuitry 22 may include radio-frequency transceiver circuitry such as wireless local area network transceiver circuitry configured to support communications over a wireless local area network link, near-field communications transceiver circuitry configured to support communications over a near-field communications link, cellular telephone transceiver circuitry configured to support communications over a cellular telephone link, or transceiver circuitry configured to support communications over any other suitable wired or wireless communications link). Wireless communications may, for example, be supported over a Bluetooth® link, a WiFi® link, a wireless link operating at a frequency between 6 GHz and 300 GHz, a 60 GHz link, or other millimeter wave link, cellular telephone link, wireless local area network link, personal area network communications link, or other wireless communications link. Device 10 may, if desired, include power circuits for transmitting and/or receiving wired and/or wireless power and may include batteries or other energy storage devices. For example, device 10 may include a coil and rectifier to receive wireless power that is provided to circuitry in device 10.

Device 10 may include input-output devices such as devices 24. Input-output devices 24 may be used in gathering user input, in gathering information on the environment surrounding the user, and/or in providing a user with output.

Devices 24 may include media playback devices such as speakers 14 and/or displays. Sensors 16 in input-output devices 24 may include one or more skin sensors 26 that detect the presence of human skin. Skin sensors 26 may use optical measurements involving two or more probe wavelengths. Because skin has an identifiable reflection spectrum, optical measurements with a skin sensor can differentiate between the presence of skin and other (non-skin) target objects.

If desired, sensors 16 may include force sensors (e.g., strain gauges, capacitive force sensors, resistive force sensors, etc.), audio sensors such as microphones, touch and/or proximity sensors such as capacitive sensors (e.g., a two-dimensional capacitive touch sensor integrated into a display, and/or a touch sensor that forms a button, trackpad, or other input device not associated with a display), and other sensors. If desired, sensors 16 may include optical sensors such as optical sensors that emit and detect light, ultrasonic sensors, optical touch sensors, optical proximity sensors, and/or other touch sensors and/or proximity sensors, monochromatic and color ambient light sensors, image sensors, fingerprint sensors, temperature sensors, sensors for measuring three-dimensional non-contact gestures ("air gestures"), pressure sensors, sensors for detecting position, orientation, and/or motion (e.g., accelerometers, magnetic sensors such as compass sensors, gyroscopes, and/or inertial measurement units that contain some or all of these sensors), health sensors, radio-frequency sensors, depth sensors (e.g., structured light sensors and/or depth sensors based on stereo imaging devices that capture three-dimensional images), optical sensors such as self-mixing sensors and light detection and ranging (lidar) sensors that gather time-of-flight measurements, humidity sensors, moisture sensors, gaze tracking sensors, and/or other sensors. In some arrangements, device 10 may use sensors 16 and/or other input-output devices to gather user input. For example, buttons may be used to gather button press input, touch sensors overlapping displays can be used for gathering user touch screen input, touch pads may be used in gathering touch input, microphones may be used for gathering audio input, accelerometers may be used in monitoring when a finger contacts an input surface and may therefore be used to gather finger press input, etc.

If desired, electronic device 10 may include additional components (see, e.g., other devices 18 in input-output devices 24). The additional components may include haptic output devices, light-emitting diodes for status indicators, light sources such as light-emitting diodes that illuminate portions of a housing and/or display structure, other optical output devices, and/or other circuitry for gathering input and/or providing output. Device 10 may also include a battery or other energy storage device, connector ports for supporting wired communication with ancillary equipment and for receiving wired power, and other circuitry.

Figure 2:
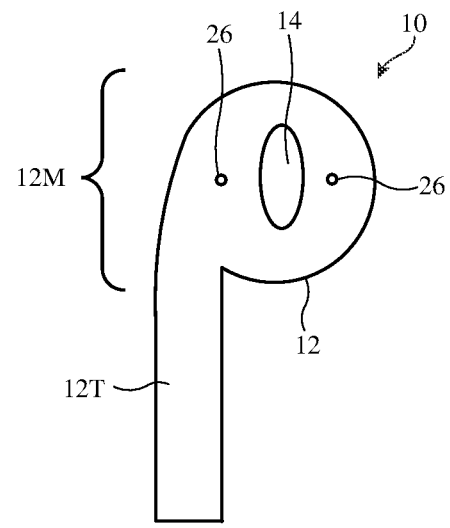
FIG. 2 is a front view of an illustrative earbud in accordance with an embodiment.

FIG. 2 is a front view of device 10 in an illustrative configuration in which device 10 is an earbud configured to be worn in a user's ear. Earbud 10 of FIG. 2 has a housing such as housing 12 formed from polymer, metal, glass, ceramic, fabric, and/or other materials. Housing 12 may include main body portion 12M and an optional protruding stalk portion 12T. Portion 12M is configured to be received in a user's ear so that a user may listen to audio (sound) presented by speaker 14. Control circuitry 20 can control audio playback (e.g., by initiating and halting sound output) based on the detected location of device 10 (e.g., in a user's ear, in a pocket, resting on a table, etc.). For example, audio can be turned off when device 10 is on a table or in a pocket or other enclosure and can be turned on only when device 10 is being worn in a user's ear adjacent to the user's skin.

To differentiate between scenarios in which device 10 is resting adjacent to fabric in a pocket or other inanimate object from scenarios in which device 10 is being worn in a user's ear, device 10 may have one or more skin sensors 26. Sensors 26 may be optical sensors that operate through transparent housing walls in portion 12M and/or that operate through openings in housing walls or localized transparent window structures.

Skin sensors 26 may be formed on one or more sides of device 10 to detect when device 10 is in a user's ear. In an illustrative configuration, skin sensors 26 include a first skin sensor on one side of portion 12M that faces a user's concha when device 10 is in a user's ear and include a second skin sensor on another side of portion 12M that faces a user's tragus when device 10 is in a user's ear. Arrangements in which multiple sensors 26 are used may help device 10 distinguish between scenarios in which device 10 is in a user's ear and in which device 10 is out of a user's ear. If desired, other configurations may be used. For example, device 10 may have only a single skin sensor that measures only the concha, only the tragus, or only another portion of the user's ear.

Figure 3:
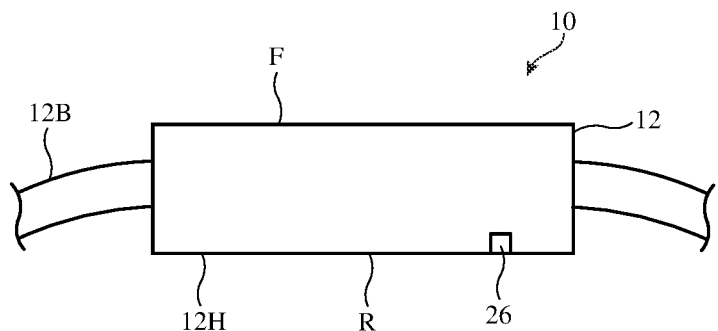
FIG. 3 is a side view of an illustrative view of an illustrative wristwatch in accordance with an embodiment.

FIG. 3 is a side view of device 10 in an illustrative configuration in which device 10 is a wristwatch device configured to be worn on a wrist of a user. In the example of FIG. 3, device 10 has housing 12. Housing 12 includes main unit 12H and strap (band) 12B. A display or other input-output device 24 may be mounted on front face F of housing portion 12H. Skin sensor may be mounted on opposing rear face R of housing portion 12M, on a portion of strap 12B, or elsewhere in housing 12. When device 10 is worn on a user's wrist, skin sensor 26 of FIG. 3 may be used to detect the presence of the user's wrist.

Figure 4:
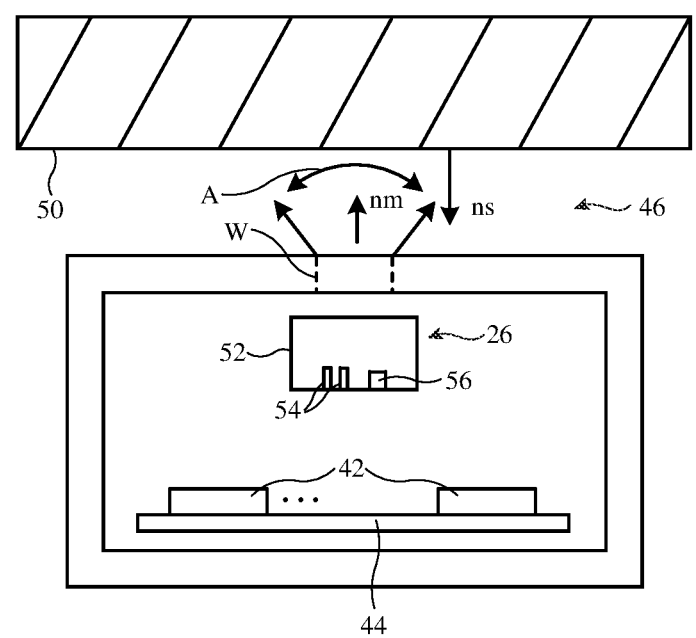
FIG. 4 is a cross-sectional side view of an illustrative electronic device with an optical skin sensor in accordance with an embodiment.

FIG. 4 is a cross-sectional side view of an illustrative electronic device with a skin sensor (sometimes referred to as a skin sensor module). In the example of FIG. 4, device 10 has housing 12. Housing 12 has structures such as walls that separate exterior region 46 from interior region 40. Electrical components 42 (e.g., control circuitry 20, communications circuitry 22, and input-output devices 24) may be mounted in interior region 40 (e.g., using one or more printed circuits such as printed circuit 44).

The electrical components mounted in interior region 40 may include one or more skin sensors such as skin sensor 26. Skin sensor 26 may have a package such as package 52. Two or more light-emitting devices 54 may be mounted in package 52 and one or more photodetectors such as photodetector 56 may be mounted in package 52 (e.g., an opaque polymer package or a package formed from other materials). Openings in the portion of the package housing wall on top of package 52 allow light emitted by devices 54 to exit package 52.

As shown in FIG. 4, package 52 may be aligned with a transparent portion of housing 12 such as portion W (e.g., a through hole, an inserted clear window, a transparent housing material that forms part of a housing wall, or other area through which light may pass). Portion W is transparent to light at the wavelengths emitted by devices 54. In an illustrative arrangement, this light is infrared light (e.g., near infrared light at wavelengths between 900 nm and 2000 nm, as an example). Infrared light is invisible to users and is therefore not distracting. If desired, visible wavelengths and/or other infrared wavelengths may be used. There may be two devices 54 in sensor 26 each of which emits light at a different respective wavelength or, if desired, there may be three or more devices 54 emitting light at different respective wavelengths (e.g., for more spectral measurement accuracy). Illustrative arrangements in which sensor 26 has a pair of devices 54 emitting light at respective first and second wavelengths of, respectively 1065 nm (corresponding to a high skin reflectance) and 1465 nm (corresponding to a lower skin reflectance) are sometimes described herein as an example.

After passing through transparent portion W (sometimes referred to as a window or transparent region), the light emitted by sensor 26 may reflect off of nearby objects such as illustrative target object 50. Reflected light from object 50 will again pass through window W and will be detected by photodetector 56 in skin sensor 26.

The emitted light from sensor 26 is emitted in direction nm (which may be, for example, the surface normal of the upper planar surface of sensor 26) while spreading over a cone characterized by angular size A (e.g., an angular spread of +/−A/2). Light sensor 56 may likewise be pointed in direction nm.

When direction nm is parallel to surface normal ns of the surface of object 50, geometric effects from tilting will not tend to impact the amount of emitted light that is reflected back towards sensor 26. Sensor 26 can therefore make accurate measurements of the relative intensity of the reflected light at each wavelength of interest (e.g., at 1065 nm and at 1465 nm). If, however, direction nm and direction ns are not parallel (e.g., when device 12 and sensor 26 are tilted with respect to the surface of the skin or other object being measured), there is a potential that geometrical effects will unevenly impact the amount of reflected light from one of light-emitting devices 54 versus the amount of reflected light from the other of light-emitting devices 54. This effect is exacerbated when the size of angle A is large, giving rise to a risk that geometrical light collection efficiency effects will obscure underlying spectral reflectivity effects.

Figure 5:
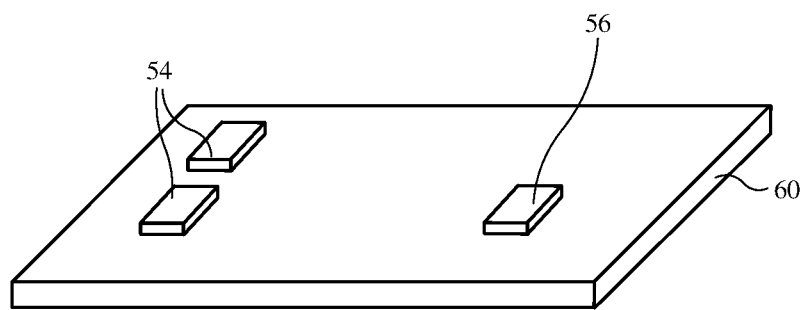
FIG. 5 is a perspective view of an illustrative printed circuit on which a pair of light sources of first and second respective wavelengths and a corresponding photodetector have been mounted in accordance with an embodiment.

To ensure that accurate spectral reflectance measurements can be made over a wide range of tilt angles, sensor 26 may be provided with an optical structure that helps to narrow the angular spread of emitted light such as a bandpass filter. Consider, as an example, the arrangement of FIGS. 5 and 6. FIG. 5 is a perspective view of an illustrative printed circuit on which components for sensor 26 have been mounted. In the example of FIG. 5, first and second light-emitting devices 54 have been mounted at one side of printed circuit 60 and photodetector 56 has been mounted on another side of printed circuit 60. Devices 54 and 60 may be semiconductor devices. As an example, devices 54 may be light-emitting diodes and photodetector 56 may be a photodiode. Other arrangements may be used, if desired. For example, devices 54 may be lasers (e.g., vertical cavity surface emitting lasers or other laser diodes).

Figure 6:
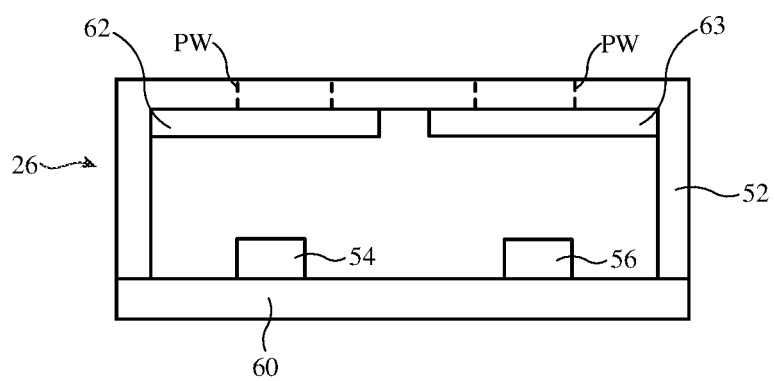
FIG. 6 is a cross-sectional side view of an illustrative skin sensor that includes the printed circuit and components of FIG. 5 in accordance with an embodiment.

FIG. 6 is a cross-sectional side view of printed circuit 60 of FIG. 5 mounted in sensor package 52. As shown in FIG. 6, package 52 may have transparent package portions PW (e.g., through-hole openings, clear portions of the walls of package 52, inserted transparent window members, etc. Devices 54 may be configured to emit light through a first of portions PW and photodetector 56 may be configured to receive reflected light through a second of portions PW.

Bandpass filter 62 may have first and second areas with first and second bandpass filters each with a respective passband for a corresponding emitted wavelength from one of devices 54. For example, in a configuration in which there are two devices 54 that emit light at two respective wavelengths (e.g., when sensor 26 is a dual-wavelength skin sensor), bandpass filter 62 may have a first region with a first bandpass filter having a first pass band that is aligned with the first wavelength of light emitted by a first of devices 54 and may also have a second region with a second bandpass filter having a second pass band that is aligned with the second wavelength of the light emitted by a second of devices 54. In another illustrative configuration, filter 62 may be formed from a single coating (e.g., a stack of thin-film layers forming a thin-film interference filter) that exhibits pass bands at both the first and second wavelengths. Configurations in which filter 62 has separate first and second areas with respective first and second bandpass filters are sometimes described herein as an example.

Filter 63 may overlap photodetector 56 and may be formed from a stack of thin-film layers that form a dual-band bandpass filter (e.g., a thin-film interference filter formed from a stack of thin-film dielectric layers of with refractive index values and thicknesses selected to form first and second passbands to pass reflected light at the first and second wavelengths) or may have another configuration that allows reflected light from the target object at the first and second wavelengths to pass to photodetector 56 (e.g., two side-by-side bandpass filters with respective first and second passbands, etc.). Filters 62 and 63 may be formed from separate substrates or may be formed from coatings deposited and patterned onto a single substrate.

By covering photodetector 56 with filter 63, extraneous ambient light will be blocked (e.g., light at wavelengths other than 1065 nm and 1465 nm will be rejected, allowing photodetector 56 to measure only light from the first of devices 54 or the second of devices 54 and not stray ambient light at other wavelengths). To distinguish between measurements associated with the first of devices 54 and measurements associated with the second of devices 54, the first and second devices can emit light at different times (e.g., using time-division multiplexing). As an example, the first and second devices can emit light in alternation. The measurements of photodetector 56 can then be synchronized to the emitted light pattern so that separate measurements for the first and second wavelengths can be made.

Figure 7:
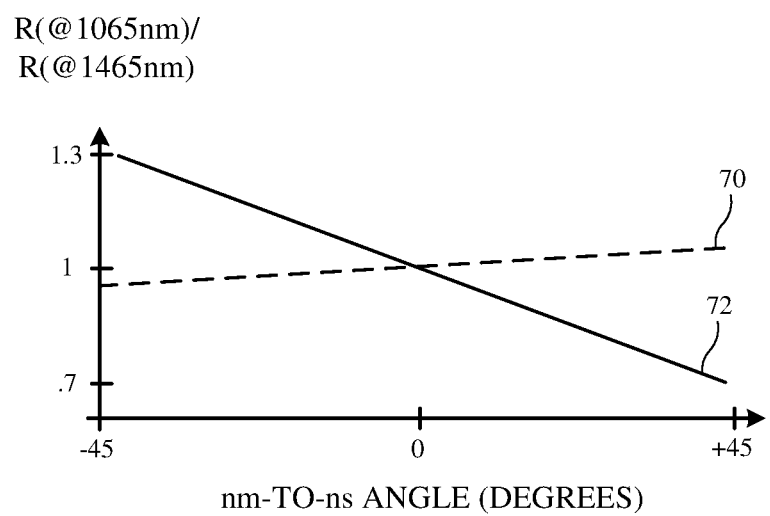
FIG. 7 is a graph showing how skin sensor measurements may be more or less susceptible to tilt-induced variations in accordance with embodiments.

The presence of bandpass filter 62 over devices 54 helps to narrow the light emission angles (cone spread angles) of the light beams emitted from devices 54. The narrowing of the angular spread of the emitted light reduces tilt dependencies in the reflected light measurements and thereby helps ensure that skin sensor 26 can make accurate measurements. FIG. 7 is a graph which illustrates the impact of narrowing the light emission cone from skin sensor 26. During operation of skin sensor 26, the ratio R of the amount of light reflected at 1065 nm to the amount of light reflected at 1465 nm is computed and compared to a threshold TH (e.g., a threshold value of 2 or other suitable value). When R is less than TH, control circuitry 20 can conclude that target object 50 is not skin, whereas when R is greater than TH, control circuitry 20 can conclude that target object 50 is skin. Dashed line 70 shows how the value of R for an illustrative target 50 that has an on-axis R value of about 1 is relatively insensitive to the amount of tilt between skin sensor 26 and the target (e.g., R varies by less than 10% or less than 5% while the angle between skin sensor light emission direction nm and surface normal ns of the illuminated surface of target 50 changes from +45° to −45°). This is due to the relatively narrow value of cone emission angle A that arises from use of bandpass filter 62. As an example, when bandpass filter 62 is present, the value of A may be less than 60° (e.g., the emitted light may be characterized by an angular spread of less than +/−30°), less than 50°, or less than 40° (e.g., light may be emitted over a range of less than −20° to +20°). In the absence of filter 62 and a resulting larger emitted light spread (e.g., 120°), geometric effects could cause the value of R to vary by a relatively large amount when tilted as shown by line 72, which could cause skin measurements to be less accurate than desired.

Figure 8:
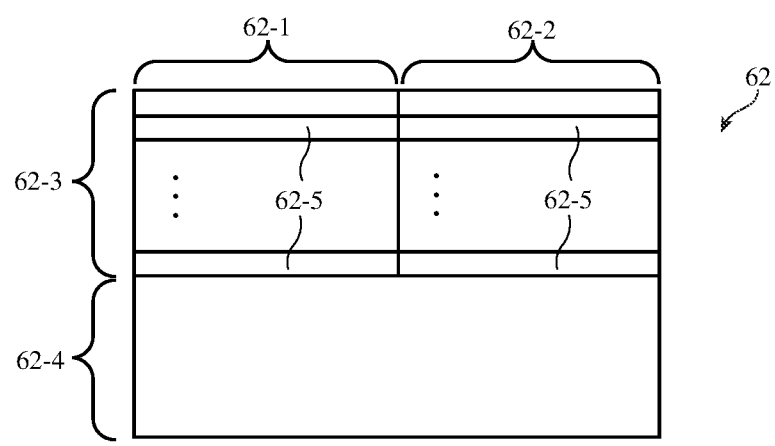
FIG. 8 is a cross-sectional side view of an illustrative thin-film interference filter that may be used in a skin sensor in accordance with an embodiment.

FIG. 8 is a cross-sectional side view of an illustrative bandpass filter for skin sensor 26. In the example of FIG. 8, bandpass filter 62 is configured to pass light at first and second passbands. Arrangements in which bandpass filter 62 has three or more pass bands may be used, if desired.

As shown in FIG. 8, filter 62 has a stack of layers 62-5 on substrate 62-4. Substrate 62-4 may be formed from glass, ceramic, polymer, semiconductor, crystalline material such as a sapphire, other material, and/or combinations of these materials. Layers 62-5 may be stacked on substrate 62-4 to form thin-film coating layer 62-3. Layers 62-5 may be formed from dielectric, semiconductor, and/or metal that is transparent at the operating wavelengths of skin sensor 26 (e.g., 1065 nm and 1465 nm in this example). In an illustrative configuration, layers 62-5 may be dielectric layers such as layers of oxide or nitride (e.g., silicon oxide, aluminum oxide, zirconium oxide, titanium oxide, silicon nitride, etc.). In general, any suitable organic or inorganic dielectric materials and/or other materials may be used in forming stacks of layers 62-5 on substrate 62-4.

Layers 62-5 may be thin-film layers formed by physical vapor deposition and other thin-film material deposition techniques. Layers 62-5 may have subwavelength thicknesses and may be configured (e.g., by selection of thickness values and/or refractive index values) to form the pass bands of filter 62 in accordance with thin-film interference filter principals.

In the example of FIG. 8, coating 62-3 has two parts, which correspond to the two separate areas overlapping respective first and second devices 54. The two separate areas form first bandpass filter 62-1, which overlaps a first of devices 54, and adjacent second bandpass filter 62-2, which overlaps a second of devices 54.

In this type of thin-film interference filter, the values of refractive index for layers 62-5 in each filter may alternate (e.g., between higher and lower values). There may be any suitable numbers of layers 62-5 in each portion of layer 62-3 (e.g., at least 30, at least 40, at least 100, 20-300, fewer than 500, fewer than 250, fewer than 100, etc.). The layers of filter 62-1 form a first bandpass filter (e.g., a filter with a 1065 nm pass band suitable for overlapping the 1065 nm light-emitting device) and the layers of filter 62-2 form a second bandpass filter (e.g., a filter with a 1465 nm pass band suitable for overlapping the 1465 nm light-emitting device).

Figure 9:
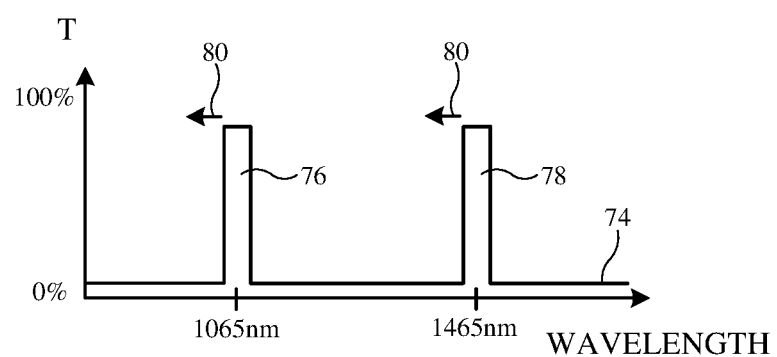
FIG. 9 is a graph in which light transmission has been plotted as a function of wavelength for an illustrative bandpass filter in accordance with an embodiment.

FIG. 9 is a graph of the transmission spectrum of an illustrative bandpass filter. Curve 74 represents the transmission T of filter 62 as a function of wavelength. As shown in FIG. 9, curve 74 has a first pass band 76 centered at 1065 nm (formed by the first bandpass filter 62-1, which is overlapping the 1065 nm light-emitting device) and a second passband 78 centered at 1465 nm (formed by the second bandpass filter 62-2, which is overlapping the 1465 nm light-emitting device). The full width half maximum (FWHM) of the light emitted by devices 54 may be 30-150 nm (as an example). In this configuration, the FWHM of each pass band may have a value in the range of 30-150 nm. The position of curve 74 in FIG. 9 corresponds to the filter characteristics of filter 62 at normal incidence (light passing through filter 62 parallel to direction nm, which is perpendicular to the planar surface of filter 62). The passbands will shift to lower wavelengths (see, e.g., shift direction 80 of FIG. 9) for light at different off-axis orientations. In general, emitted light rays that have greater angles with respect to direction nm will exhibit greater shifts, resulting in significant attenuation for those light rays as the passbands moves away from its nominal position. On-axis light rays (e.g., light rays in a narrow cone surrounding direction nm) will not be affected and will continue to be passed through pass bands 76 and 78. As a result of these properties, bandpass filter 62 will pass on-axis light rays and will block off-axis light rays, resulting in a narrowing of the angular spread of the light rays in the emitted cone of light from devices 54 as this light passes through filter 62.

Figure 10:
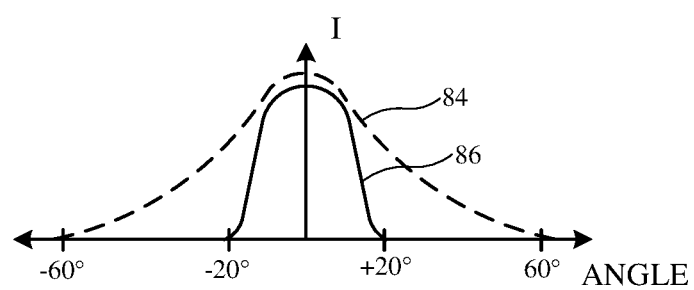
FIG. 10 is a graph of output intensity versus output angle for illustrative skin sensors with and without bandpass filters overlapping their light-emitting devices in accordance with an embodiment.

FIG. 10 is a graph showing how the presence of filter 62 helps narrow the range of emitted light angles for the light emitted by devices 54. Dashed curve 84 corresponds to the nominal output of light-emitting devices 54 in the absence of filter 62. In this example, there is a 120° angular spread (e.g., a wide Lambertian distribution extending +/−60° with respect to direction nm) of emitted light intensity. This wide range of emitted light angles can lead to undesired tilt angle dependencies when measuring target objects as described in connection with curve 72 of FIG. 7. When filter 62 is present in skin sensor 26 (e.g., when filter 62 overlaps devices 54 and filters the light emitted from devices 54), the range of angles covered by each beam of emitted light is reduced (see, e.g., narrowed curve 86, which, in this example is characterized by a 40° angular spread, which is significantly narrower than the uncorrected 120° output from devices 54 when not filtering is present). This narrowing of the emitted light from skin sensor 26 may effectively remove tilt angle dependencies and thereby help to enhance the accuracy of skin reflectivity measurements.

If desired, other narrowing arrangements may be used in addition to (or instead of) using bandpass filter 64. For example, devices 54 may be provided with narrow angular emission characteristics (e.g., when devices 54 are lasers or resonant cavity light-emitting diodes), apertures PW in the top of package 52 may be narrowed to restrict the beamwidth of emitted light, a lens, light pipe, and/or other optical elements may be used to restrict emitted beam width, and/or other structures may be added to sensor 26 to help restrict the angular spread of emitted light and/or otherwise reduce tilt dependence in the measured values of R for sensor 26. If desired, a diffuser may be formed on filter 62 or may be incorporated into sensor 26 in place of filter 62 to help reduce tilt dependence in the measured values of R.

Thin-film interference filter coatings such the coating for filter 62-3 of FIG. 8 may be formed by depositing layers 62-5 by physical vapor deposition or other thin-film-layer deposition techniques and patterning using photolithography (lift-off, etching, etc.), shadow masking, and/or other suitable patterning techniques. Illustrative fabrication operations for filter 62 are illustrated in FIGS. 11, 12, 13, 14, and 15.

Figure 11:
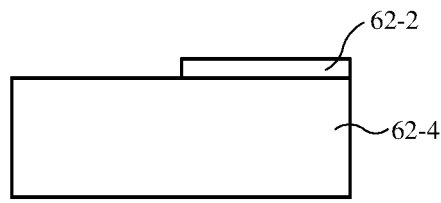
FIGS. 11, 12, 13, 14, and 15 show illustrative operations involved in forming bandpass filters in accordance with embodiments.

As shown in FIG. 11, with one illustrative arrangement, filter 62-2 may be deposited by depositing and patterning a photoresist layer on the left side of substrate 62-4 followed by deposition of the layers of filter 62-2 and lift-off to remove the left-hand portion of the deposited layers. This leaves filter 62-2 of FIG. 11 on substrate 62-4.

Figure 12:
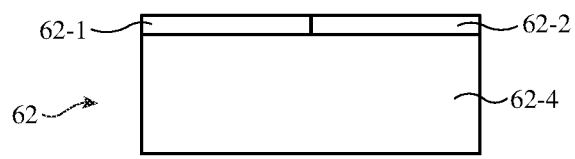

As shown in FIG. 12, this lift-off patterning technique can then be repeated to form filter 62-1 adjacent to filter 62-2. First, photoresist is deposited and patterned to cover filter 62-2 while leaving the left half of substrate 62-4 uncovered. Second, the layers of filter 62-1 are deposited. Third, using lift-off, the portion of the layers of filter 62-1 that overlap filter 62-2 are removed, leaving filters 62-1 and 62-2 on adjacent portions of substrate 62-4, as shown in FIG. 12.

Figure 13:
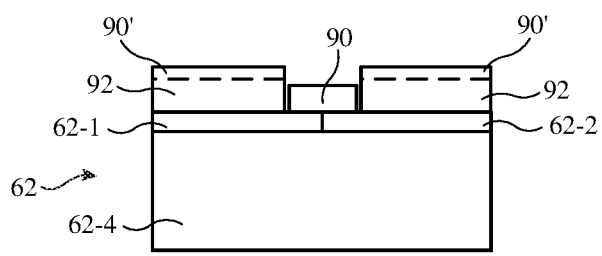

It may be desirable to form an opaque masking layer on the upper and/or lower surfaces of filter 62. This opaque masking layer may run along the seam between filters 62-1 and 62-1, where filter structures may overlap (and may therefore not be exhibiting their desired optical characteristics). In the example of FIG. 13, a strip of black ink or other opaque material (opaque masking strip 90) has been formed on the surface of filter 62 covering the seam between filters 62-1 and 62-2. To form strip 90, photoresist 92 was deposited and patterned to leave a gap for strip 90. An opaque masking layer was then deposited as a blanket film (see, e.g., portions 90' of the film, which cover photoresist 92, and strip 90, which is deposited in the gap). Following lift-off operations, photoresist 92 and portions 90' are removed, leaving only strip 90.

Figure 14:
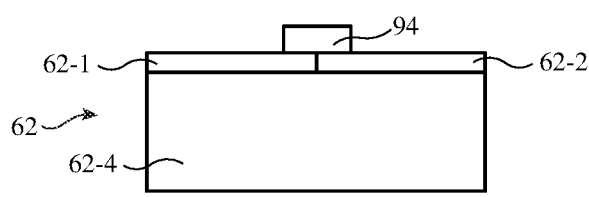
Figure 15:
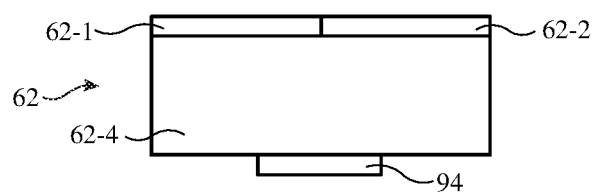

In the example of FIGS. 14 and 15, ink-jet printing, pad printing, or other printing techniques have been used to deposit opaque masking strip 94 (e.g., a layer of black ink). In the example of FIG. 14, strip 94 has been formed by printing a strip of black ink on the surface of filter 62 running along the seam between filters 62-1 and 62-2. In the example of FIG. 15, strip 94 has been printed on the exposed lower surface of substrate 62-4 so as to overlap and run along the seam between filters 62-1 and 62-2 formed on the opposing front side of filter 62.

The foregoing is merely illustrative and various modifications can be made to the described embodiments. The foregoing embodiments may be implemented individually or in any combination.

What is claimed is:

1. A skin sensor configured to detect a presence of skin using reflectance measurements from a target at a first wavelength and at a second wavelength at which skin reflects less than at the first wavelength, comprising:
   a first light-emitting device configured to emit light at the first wavelength;
   a second light-emitting device configured to emit light at the second wavelength;
   a first bandpass filter that has a first pass band at the first wavelength and that overlaps the first light-emitting device;
   a second bandpass filter that has a second pass band at the second wavelength and that overlaps the second light-emitting device, wherein the second bandpass filter meets the first bandpass filter at a seam, and wherein the emitted light at the first and second wavelengths that has passed respectively through the first and second bandpass filters is characterized by an angular spread of less than +/−30°;
   an opaque masking layer that overlaps a portion of the first bandpass filter, a portion of the second bandpass filter, and the seam; and
   a photodetector configured to measure the emitted light at the first wavelength after passing through the first bandpass filter and reflecting from the target and configured to measure the emitted light at the second wavelength after passing through the second bandpass filter and reflecting from the target.

2. The skin sensor defined in claim 1 wherein the first and second bandpass filters are formed on a common substrate.

3. The skin sensor defined in claim 2 wherein the first and second bandpass filters are thin-film interference filters.

4. The skin sensor defined in claim 3 wherein the first light-emitting device comprises a first infrared light-emitting device and wherein the second light-emitting device comprises a second infrared light-emitting device.

5. The skin sensor defined in claim 4 wherein the first infrared light-emitting device comprises a 1065 nm light-emitting diode and wherein the second infrared light-emitting device comprises a 1465 nm light-emitting diode.

6. The skin sensor defined in claim 1 further comprising a filter overlapping the photodetector that is configured to pass light at the first and second wavelengths.

7. The skin sensor defined in claim 1 further comprising a printed circuit on which the first and second light-emitting devices and the photodetector are mounted.

8. The skin sensor defined in claim 7 further comprising a package with a first aperture aligned with the first and second light-emitting devices through which the emitted light at the first and second wavelengths passes and a second aperture aligned with the photodetector.

9. The skin sensor defined in claim 1 wherein the first and second light-emitting devices are infrared light-emitting devices.

10. The skin sensor defined in claim 9 wherein the first and second light-emitting devices comprise infrared light-emitting diodes.

11. An earbud, comprising:
an earbud housing;
a speaker in the earbud housing;
a skin sensor in the earbud housing, wherein the speaker is configured to output sound at least partly in response to detection of skin with the skin sensor and wherein the skin sensor comprises:
a first light-emitting device configured to emit light at a first wavelength;
a second light-emitting device configured to emit light at a second wavelength;
a thin-film interference filter overlapping the first and second light-emitting devices that has a first area with a first pass band that is aligned with the first wavelength and that has a second area with a second pass band that is aligned with the second wavelength, wherein the first and second areas are formed on a shared substrate that overlaps the first and second light-emitting devices; and
a photodetector configured to detect reflected light at the first and second wavelengths.

12. The earbud defined in claim 11 wherein the thin-film interference filter has a substrate, a first bandpass filter on the first area of the substrate configured to pass light in the first pass band, and a second bandpass filter on the second area of the substrate configured to pass light in the second pass band.

13. The earbud defined in claim 11 wherein the first light-emitting device comprises a first infrared light-emitting device and wherein the second light-emitting device comprises a second infrared light-emitting device.

14. The earbud defined in claim 13 wherein the first infrared light-emitting device comprises a 1065 nm light-emitting device.

15. The earbud defined in claim 14 wherein the second infrared light-emitting device comprises a 1465 nm light-emitting device.

16. The earbud defined in claim 15 wherein the 1065 nm light-emitting device comprises a 1065 nm light-emitting diode and wherein the 1465 nm light-emitting device comprises a 1465 nm light-emitting diode.

* * * * *